United States Patent [19]  [11] 4,153,703
Harrison et al.  [45] May 8, 1979

[54] METHOD OF CONTROLLING INSECTS AND ACARIDS WITH CERTAIN ARYL-SUBSTITUTED THIAZOLES

[75] Inventors: William A. Harrison, Guelph, Canada; Winchester L. Hubbard, Woodbridge; Robert E. Grahme, Jr., Cheshire, both of Conn.; James N. Tousignant, Guelph, Canada

[73] Assignees: Uniroyal, Inc., New York, N.Y.; Uniroyal Ltd., Ontario, Canada

[21] Appl. No.: 811,648

[22] Filed: Jun. 30, 1977

[51] Int. Cl.² .................... A01N 9/12; A01N 9/22
[52] U.S. Cl. .................... 424/270; 260/302 R; 424/263
[58] Field of Search .................... 424/270; 260/302 R

[56] References Cited

U.S. PATENT DOCUMENTS

| 1,970,656 | 8/1934 | Johnson | 260/302 R |
| 2,014,498 | 9/1935 | Johnson | 260/302 R |
| 2,870,158 | 1/1959 | Asinger et al. | 260/302 R |
| 3,506,679 | 4/1970 | Cavalla et al. | 260/302 |
| 3,661,920 | 5/1972 | Hepworth et al. | 424/270 |
| 3,705,153 | 12/1972 | Kaneko et al. | 424/270 |
| 3,749,787 | 7/1973 | Hepworth et al. | 424/270 |
| 3,769,413 | 10/1973 | Kupfer et al. | 424/270 |
| 3,821,237 | 6/1974 | Malen et al. | 260/302 R |
| 3,833,601 | 9/1974 | Beck et al. | 424/270 |

FOREIGN PATENT DOCUMENTS

| 950825 | 7/1974 | Canada. | |
| 1173097 | 7/1964 | Fed. Rep. of Germany | 260/302 R |
| 2125193 | 11/1972 | Fed. Rep. of Germany | 260/302 R |
| 1193148 | 5/1970 | United Kingdom | 260/302 R |

Primary Examiner—Allen J. Robinson
Attorney, Agent, or Firm—James J. Long

[57] ABSTRACT

The use of di- and triaryl-substituted thiazoles as pesticides is disclosed. Insects, such as mosquitos, and acarids, such as mites and ticks, are among the pests which may be controlled.

5 Claims, No Drawings

METHOD OF CONTROLLING INSECTS AND ACARIDS WITH CERTAIN ARYL-SUBSTITUTED THIAZOLES

This invention relates to a method of controlling pests. More specifically, it relates to a method for controlling insects and acarids using aryl-substituted thiazoles.

Substituted thiazoles have been previously described in the literature. For example, U.S. Pat. No. 3,506,679 (Apr. 14, 1970) discloses certain thiazoles having anti-inflammatory properties. French Pat. No. 1,587,945 (Feb. 23, 1970) discloses certain thiazoles having similar properties. Canadian Pat. No. 950,825 (July 9, 1974) discloses the use of 2-(3-pyridyl)thiazoles as insecticides. Nothing in the literature, however, discloses the pesticidal use of the compounds of this invention.

Mites and ticks are examples of acarids. Plant-feeding mites cause substantial agricultural crop losses. Crops such as alfalfa, apples, corn, cotton, grapes, oranges, potatoes, sorghum, and peanuts may be completely destroyed by these pests.

Ticks and some mites suck the blood of men and animals. Many diseases are transmitted by the bites of these pests, such as Rocky Mountain spotted fever, relapsing fever, and tularemia.

Various insects, such as weevils and aphids, also cause extensive crop losses, and others, such as flies and mosquitoes, spread disease among men and animals.

Thiazoles have the following structure

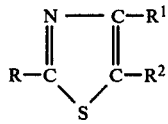

wherein R, $R^1$, and $R^2$ are hydrogen or substituted groups.

The compounds of this invention are di- and triaryl-substituted thiazoles. "Aryl" should be understood to include naphthyl, phenyl, pyridyl, and biphenylyl groups as well as their alkyl, halo, amino, alkoxy, alkylenedioxy, and hydroxy substituted analogues. In the case of diarylthiazoles, R, $R^1$, or $R^2$, as the case may be, can be hydrogen, an alkyl, or a nitro group.

More specifically, the compounds of this invention are those having the thiazole structure, shown above, wherein R is phenyl, naphthyl, pyridyl, alkaryl, alkoxyaryl, alkylenedioxyaryl, aminoaryl, alkaminoaryl, haloaryl, or hydroxyaryl; $R^1$ is hydrogen, alkyl, phenyl, biphenylyl, aminoaryl, alkaminoaryl, alkaryl, alkoxyaryl, alkylenedioxyaryl, or haloaryl; and $R^2$ is hydrogen, alkyl, phenyl, alkoxyaryl, alkylenedioxyaryl, haloaryl, or nitro; provided that at least one of $R^1$ and $R^2$ is aromatic, and that if R is alkoxyaryl or alkylenedioxyphenyl, $R^1$ is aromatic.

Usually, R is phenyl, naphthyl, pyridyl, alkylphenyl having 7 to 14 carbon atoms, alkoxyphenyl having 7 to 14 carbon atoms, alkylenedioxyphenyl having 7 to 14 carbon atoms, aminophenyl or alkaminophenyl having 6 to 14 carbon atoms, halophenyl, or hydroxyphenyl; $R^1$ is hydrogen, alkyl having 1 to 5 carbon atoms, phenyl, biphenylyl, aminophenyl or alkaminophenyl having 6 to 14 carbon atoms, alkylphenyl having 7 to 14 carbon atoms, alkoxyphenyl having 7 to 14 carbon atoms, alkylenedioxyphenyl having 7 to 14 carbon atoms, or halophenyl; and $R^2$ is hydrogen, alkyl having 1 to 5 carbon atoms, phenyl, alkoxyphenyl having 7 to 14 carbon atoms, alkylenedioxyphenyl having 7 to 14 carbon atoms, halophenyl, or nitro; provided that at least one of $R^1$ and $R^2$ is aromatic, and that if R is alkoxyphenyl or alkylenedioxyphenyl, $R^1$ is aromatic.

Preferred are those compounds having the thiazole structure, shown above, wherein R is phenyl, naphthyl, pyridyl, alkylphenyl having 7 to 9 carbon atoms, alkoxyphenyl having 7 to 9 carbon atoms, methylenedioxyphenyl, aminophenyl or alkaminophenyl having 6 to 8 carbon atoms, chlorophenyl, or hydroxyphenyl; $R^1$ is hydrogen, methyl, ethyl, phenyl, biphenylyl, aminophenyl or alkaminophenyl having 6 to 8 carbon atoms, alkylphenyl having 7 to 9 carbon atoms, alkoxyphenyl having 7 to 8 carbon atoms, methylenedioxyphenyl, chlorophenyl, or bromophenyl; and $R^2$ is hydrogen, methyl, phenyl, methoxyphenyl, methylenedioxyphenyl, chlorophenyl, or nitro; provided that at least one of $R^1$ and $R^2$ is aromatic, and that if R is alkoxyphenyl or alkylenedioxyphenyl, $R^1$ is aromatic.

Most preferred are the thiazoles having the following assigned numbers in Table I, below: 1, 2, 4, 6, 17, 36, and 43 (which are known in the art) and numbers 3, 5, 12, 15, 31, 32, 46, and 64 (which are new).

The compounds of this invention may be used alone or they may be combined with a solid or liquid carrier. The carrier may contain surface active agents or diluents which enhance the effectiveness of the active agent or facilitate handling. The materials are applied to the locus of the pests, that is, the materials are applied directly to the plant to be protected or sprayed in its proximity, or sprayed onto or near the pests to be controlled.

Practical formulations may be dusts, wettable powders, or emulsifiable concentrates. They can contain from 1 to 95% of the active ingredient. Sprays may contain only a few parts per million or may be undiluted concentrates applied by ultra low volume techniques. The amount of chemical employed depends upon many factors, but normally would be from 0.1 to 10 pounds per acre. With respect to a pest, a "pesticidally effective" amount is the amount which, under the particular use conditions, results in control of the pest. The pesticidally effective amount can be readily determined by one skilled in the art within the guidelines specified.

Di- and triarylthiazoles can be made by two well-known methods. The first method involves reaction of a thioamide with an alpha-halocarbonyl compound, as shown in the following equation:

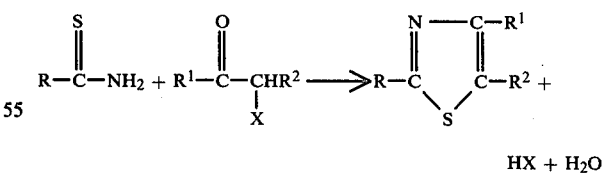

HX + $H_2O$

The preparation is carried out by heating approximately equimolar amounts of the two reactants in a solvent such as methanol, ethanol, or isopropyl alcohol. Although hydrogen halide is produced in the reaction, the product is frequently not obtained as a hydrohalide salt, unless there is a more basic site in the molecule than the thiazole nitrogen. Often the free thiazole will crystallize directly from the reaction mixture when it is cooled. If the hydrohalide salt is obtained, however, it can be isolated as such or be converted to the free base by treatment with a stronger base, such as ammonium or sodium hydroxide. If no crystals form, the reaction mixture can be evaporated and the product isolated by standard techniques.

The second method, particularly useful for making 2,5-diphenylthiazoles, involves reaction of an alpha-acylaminocarbonyl compound with phosphorus pentasulfide, as shown in the following equation:

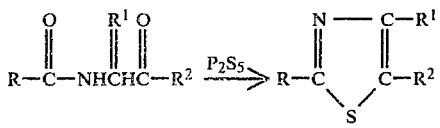

Both methods are discussed by Wiley et al., in Organic Reactions, vol. VI, p. 367 (John Wiley & Sons, Inc., New York 1951).

The following procedures describe specifically how several of the compounds of the invention are synthesized. The Compound Number is shown in Table I, below. Procedures for preparing the other compounds of this invention will be readily apparent to one skilled in the art.

Triphenylthiazole (Compound No. 6)

Thiobenzamide (13.7g, 0.10 mole) and desyl chloride (23.1g, 0.10 mole) are heated under reflux in isopropyl alcohol (100 ml) for three hours. When the reaction mixture is cooled, the white solid precipitate formed is filtered off, washed twice with isopropyl alcohol, and dried. The yield of triphenylthiazole, m.p. 84°–85.5° C., is 21.5g or 69%.

2,4-Diphenylthiazole (Compound No. 4) and 5-Nitro-2,4-diphenylthiazole (Compound No. 7)

2,4-Diphenylthiazole is prepared by reacting thiobenzamide and phenacyl bromide in ethanol, as described by Hubacher in Annalen 259, 237 (1890). This thiazole (11.7g, 0.049 mole) is then treated with glacial acetic acid (20 ml), concentrated sulfuric acid (15 ml) and fuming nitric acid (3 ml), and the mixture is heated on a steam bath for two hours. The reaction mixture is poured into cold water and the precipitated oil is extracted with chloroform. Evaporation of the chloroform leaves a semi-solid residue which is digested with ethanol. The undissolved yellow solid is collected and dried. The NMR and IR spectra of the product, which melts at 152°–154° C., shows it to be 5-nitro-2,4-diphenylthiazole. The yield is 6.0g (43%).

2,5-Diphenylthiazole (Compound No. 1)

Pyridinium hydrobromide perbromide (12g) is added to a solution of phenylacetaldehyde (12g, 0.10 mole) in glacial acetic acid (200 ml) and the mixture is stirred for one hour at room temperature. The reaction mixture is poured into water, extracted with benzene, and the benzene solution is washed with excess aqueous sodium bicarbonate. Benzene is then evaporated and the residue, crude alpha-bromophenylacetaldehyde, is dissolved in ethanol (100 ml) and reacted with thiobenzamide (13.7g). The mixture is heated under reflux for one hour, evaporated, and the residue is treated with benzene. The insoluble solid, crude 2,5-diphenylthiazole hydrobromide, is filtered off, mixed with dilute ammonium hydroxide, and then the thiazole base is extracted with chloroform. The chloroform is evaporated, and the residue is recrystallized from isopropyl alcohol to give 5.0g (21% yield) of 2,5-diphenylthiazole, m.p. 102°–105° C.

Another sample of 2,5-diphenylthiazole is prepared by reacting alpha-(benzamido) acetophenone with phosphorus pentasulfide according to the procedure given by Gabriel, Berichte 43, 137 (1910); C.A. 4, 928. The overall yield, based on phenacyl bromide, is about 25% and the product melts at 103°–106° C.

2-(2-Chlorophenyl)-4-methyl-5-phenylthiazole (Compound No. 31)

1-Bromo-1-phenyl-2-propanone (10.6g, 0.050 mole), o-chlorothiobenzamide (8.8g, 0.051 mole), and ethanol (100 ml) are mixed and, after the initial exothermic reaction has subsided, heated under reflux for two hours. The ethanol is evaporated and the residue is treated with chloroform and aqueous sodium bicarbonate. The chloroform layer is separated and evaporated to leave a yellow oil which solidifies on standing. Recrystallization from acetonitrile yields 11.3g (79%) of 2-(2-chlorophenyl)-4-methyl-5-phenylthiazole, m.p. 63°–65° C.

2-(4-Methoxyphenyl)-4,5-diphenylthiazole (Compound No. 62)

p-Thioanisamide (16.7g, 0.10 mole) and desyl chloride (23.1g, 0.10 mole) are heated under reflux in 95% ethanol (100 ml) for two hours. The reaction mixture is cooled and the white solid precipitate collected by filtration, washed with ethanol and recrystallized from ethanol-ethyl acetate. The yield of 2-(4-methoxyphenyl)-4,5-diphenylthiazole, m.p. 132°–134° C., is 26.0g or 76%. p-Thioanisamide is prepared from the corresponding nitrile by the method of Fairfull et al., J. Chem. Soc. 1952, 742.

2-(3,4-Methylenedioxyphenyl)-4,5-diphenylthiazole (Compound No. 74)

Thiopiperonylamide (18.1g, 0.10 mole) and desyl chloride (23.1g, 0.10 mole) are heated under reflux in 95% ethanol (100 ml) for two hours. An oil precipitates which solidifies when the reaction mixture is cooled. The solid is collected and recrystallized from ethanolethyl acetate to give 24.0g (67% yield) of 2-(3,4-methylenedioxyphenyl)-4,5-diphenylthiazole, m.p. 121°–124° C. Thiopiperonylamide is also prepared from the corresponding nitrile by the method of Fairfull et al., J. Chem. Soc. 1952, 742.

After preparation, the chemicals of this invention are tested to determine their pesticidal efficacy. The tests employed are described below.

Mite Contact and Residual Tests

Host plants used in this test are three-week old cotton grown in the greenhouse. Plants are trimmed to two leaves and two potted plants are used for each rate of chemical tested.

Compositions for testing are prepared by dissolving 0.1 gram of substituted thiazole in one ml of acetone to which one drop (30mg) of a polyoxyethylated vegetable oil surfactant is added. This is then dispersed in 100 ml of water to obtain a 1000 ppm concentration of aryl substituted thiazole in water. Aliquots are further diluted with water to obtain 500 and 100 ppm solutions.

In the Contact Test, adult mites (*Tetranychus urticae*, the two-spotted spider mite) are introduced into 1" (2.54 cm) diameter circles of tanglefoot on the upper leaf surfaces 48 hours prior to use. The test dispersions are sprayed onto these plants with an atomizer which gives nearly complete coverage of the foliage.

An initial count of the mites present is made immediately following spray application and a final count of live mites is made after the host plants have been kept in the greenhouse at approximately 75° F. (24° C.) for five days.

"Percent Control" is calculated and adjusted for natural mortality by adaptation of Abbott's well-known formula:

"Adjusted Percent Control" =

$$\frac{\left(\begin{array}{c}\% \text{ mites dead} \\ \text{treated plants}\end{array}\right) - \left(\begin{array}{c}\% \text{ mites dead} \\ \text{control plants}\end{array}\right)}{\left(\begin{array}{c}\% \text{ mites alive} \\ \text{control plants}\end{array}\right)} \times 100$$

A variation of this test provides one-day residual information. In this variation the mites are introduced onto the treated leaves one day after the plants are sprayed. In the same manner as for the Contact Test, counts are made both immediately after and five days after the mites are introduced, and the Adjusted Percent Control is calculated.

Mosquito Larvae Test

Test compositions are prepared by dissolving 30 mg of the thiazole in 10 ml of acetone. Dilutions are made with water to 10 ppm. Two 25 ml aliquots are placed in test tubes to which 10 to 25 larvae of the Yellow Fever Mosquito, *Aedes aegypti*, are added. The tubes are held at 20° C. for 72 hours. At the end of this period the Adjusted Percent Control is determined in the same way as for the other two tests.

Table I indicates the results of these tests on eighty-one compounds within the scope of this invention. The Contact Tests are made using 1000 ppm solutions (except for compounds 47 and 48 where 2000 ppm solutions are used). For compounds 40 and 41, Contact Tests at 500 and 100 ppm are also made. The Residual One-Day Tests are made using 500 and 1000 ppm solutions. The Mosquito Larvae Tests are made using 10 ppm solutions. A "0" indicates that the Adjusted Percent Control is zero, i.e., the treatment is ineffective. A blank space indicates that no test is performed. Compounds number 1, 2, 4, 6, 8, 9, 13, 17, 36, 43, 47, 49, 52, 61, and 68 in Table I have been previously reported in the literature, but without disclosure of any pesticidal activity.

Table I shows that of the 81 compounds, 67 are at least 75% effective in controlling mites in the Contact Test at 1000 ppm, and 61 are at least 90% effective. Twenty-eight of these 81 compounds are 75% or more effective in controlling mosquito larvae under test conditions.

As will be understood by one skilled in the art, a compound which is not highly effective at one concentration may be highly effective at another. For example, compound 41 was only 44% effective in the Contact Test at 100 ppm, but was 84% effective at 500 ppm and 98% effective at 1000 ppm. It will also be understood by one skilled in the art that one compound less effective than another in a test may still be chosen for commercial use because of more economic production, greater ease of application, etc.

TABLE 1

| | | Adjusted Percent Control | | | |
|---|---|---|---|---|---|
| Compound No. | Compound Name | Mite Contact (1000 ppm) | Mite Residual (1000 ppm) | Mite Residual (500 ppm) | Mosquito Larvae (10 ppm) |
| 1 | 2,5-diphenylthiazole | 100 | 100 | 100 | 95 |
| 2 | 4-methyl-2,5-diphenylthiazole | 100 | | 95 | 100 |
| 3 | 4-ethyl-2,5-diphenylthiazole | | | 100 | 100 |
| 4 | 2,4-diphenylthiazole | 100 | 100 | 100 | 85 |
| 5 | 5-methyl-2,4-diphenylthiazole | 100 | | 87 | 85 |
| 6 | 2,4,5-triphenylthiazole | 100 | 100 | 95 | 70 |
| 7 | 5-nitro-2,4-diphenylthiazole | 90 | 15 | 19 | 10 |
| 8 | 4-(methylphenyl)-2-phenylthiazole | 100 | | 100 | 0 |
| 9 | 4-(4-biphenylyl)-2-phenylthiazole | 90 | | | 0 |
| 10 | 4-[4-(dimethylamino)phenyl]-2,5-diphenylthiazole | 100 | 15 | 0 | 0 |
| 11 | 2-(2-methylphenyl)-4-phenylthiazole | 100 | | | 100 |
| 12 | 2-(2-methylphenyl)-4,5-diphenylthiazole | 100 | 98 | 93 | 50 |
| 13 | 2-(3-methylphenyl)-4-phenylthiazole | 95 | 100 | 64 | 100 |
| 14 | 2-(3-methylphenyl)-4,5-diphenylthiazole | 100 | 71 | 73 | 10 |
| 15 | 5-(4-chlorophenyl)-4-methyl-2-(3-methyl-)phenyl)thiazole | 100 | | 91 | 50 |
| 16 | 5-(4-chlorophenyl)-2-(3-methylphenyl)-4-phenylthiazole | 95 | 82 | 80 | 0 |
| 17 | 5-methyl-2-(4-methylphenyl)-4-phenylthiazole | 100 | | 98 | 65 |
| 18 | 5-(4-chlorophenyl)-2-(4-isopropylphenyl)-4-methylthiazole | 100 | | 96 | 0 |
| 19 | 2-(4-isopropylphenyl)-4-phenylthiazole | 97 | 80 | 67 | 0 |
| 20 | 2-(4-isopropylphenyl)-4,5-diphenylthiazole | 100 | 41 | 22 | 0 |
| 21 | 2-(2,3-dimethylphenyl)-4-phenylthiazole | 100 | | | 98 |
| 22 | 2-(2,3-dimethylphenyl)-4,5-diphenylthiazole | 100 | | | 0 |
| 23 | 2-(2,4-dimethylphenyl)-4-phenylthiazole) | 100 | | 38 | 100 |
| 24 | 2-(2,4-dimethylphenyl)-4,5-diphenylthiazole | 98 | 17 | 33 | 0 |
| 25 | 2-(2-hydroxyphenyl)-4,5-diphenylthiazole | 100 | | | 0 |
| 26 | 2-(2-aminophenyl)-4-phenylthiazole | 100 | 38 | 35 | 98 |
| 27 | 2-(2-aminophenyl)-4,5-diphenylthiazole | 100 | | | 0 |
| 28 | 2-(3-aminophenyl)-4,5-diphenylthiazole | 100 | | | 50 |
| 29 | 2-[4-(dimethylamino)phenyl]-4-phenylthiazole | 90 | 82 | 37 | 70 |
| 30 | 2-[4-(dimethylamino)phenyl]-4,5-diphenylthiazole | 90 | | | 0 |
| 31 | 2-(2-chlorophenyl)-4-methyl-5-phenylthiazole | 100 | | 100 | 95 |
| 32 | 2-(2-chlorophenyl)-4-ethyl-5-phenylthiazole | | 100 | 100 | 85 |
| 33 | 2-(4-chlorophenyl)-4-methyl-5-phenylthiazole | 100 | | 100 | 10 |
| 34 | 2-(3-chlorophenyl)-5-(4-chlorophenyl)-4-methylthiazole | 100 | | 97 | 0 |
| 35 | 2,5-bis(4-chlorophenyl)-4-methylthiazole | 100 | | 93 | 0 |
| 36 | 2-(4-chlorophenyl)-4-phenylthiazole | 100 | 100 | 98 | 80 |

TABLE 1-continued

| Compound No. | Compound Name | Adjusted Percent Control | | | |
|---|---|---|---|---|---|
| | | Mite Contact (1000 ppm) | Mite Residual (1000 ppm) | Mite Residual (500 ppm) | Mosquito Larvae (10 ppm) |
| 37 | 2-(4-chlorophenyl)-5-methyl-4-phenylthiazole | 100 | | 95 | 5 |
| 38 | 2-(2-chlorophenyl)-4,5-diphenylthiazole | 100 | 83 | 75 | 15 |
| 39 | 2-(4-chlorophenyl)-4,5-diphenylthiazole | 100 | | 46 | 95 |
| 40 | 2,5-bis(4-chlorophenyl)-4-phenylthiazole | 100* | | 0 | 15 |
| 41 | 2,4-bis(4-chlorophenyl)thiazole | 98** | | 22 | 0 |
| 42 | 5-(4-chlorophenyl)-4-methyl-2-(1-naphthyl)-thiazole | 100 | | 35 | 0 |
| 43 | 2-(1-naphthyl)-4-phenylthiazole | 100 | | 78 | 100 |
| 44 | 2-(1-napthyl)-4,5-diphenylthiazole | 90 | | | 85 |
| 45 | 4-(2,4-dimethylphenyl)-2-(1-naphthyl)-thiazole | 100 | 13 | 1 | 0 |
| 46 | 4-(4-chlorophenyl)-2-(1-naphthyl)-thiazole | 100 | 100 | 83 | 100 |
| 47 | 4-phenyl-2-(3-pyridyl)thiazole | *** | | | 20 |
| 48 | 4-phenyl-2-(3-pyridyl)thiazole hydrochloride | *** | | | 0 |
| 49 | 5-methyl-4-phenyl-2-(3-pyridyl)-thiazole | 100 | 23 | 27 | 85 |
| 50 | 4,5-diphenyl-2-(2-pyridyl)-thiazole | 100 | 94 | 92 | 0 |
| 51 | 4,5-diphenyl-2-(3-pyridyl)-thiazole | 100 | 15 | 11 | 100 |
| 52 | 4,5-diphenyl-2-(4-pyridyl)-thiazole | 75 | | | 0 |
| 53 | 4-(4-methylphenyl)-2-(3-pyridyl)-thiazole | 80 | | | 80 |
| 54 | 5-methyl-4-(4-methylphenyl)-2-(3-pyridyl)thiazole | 45 | | | 90 |
| 55 | 4-(4-biphenylyl)-2-(3-pyridyl)-thiazole | 50 | | | 0 |
| 56 | 4-(4-bromophenyl)-2-(3-pyridyl)-thiazole | 55 | | | 90 |
| 57 | 4,5-bis(4-methoxyphenyl)-2-phenyl-thiazole | 75 | | | 0 |
| 58 | 4,5-bis(3,4-methylenedioxyphenyl)-2-phenylthiazole | 40 | | | 90 |
| 59 | 4,5-bis(4-methoxyphenyl)-2-(2-methyl-phenyl)thiazole | 100 | 5 | 27 | 0 |
| 60 | 2-(4-isopropylphenyl)-4-(4-methoxy-phenyl)thiazole | 75 | | | 0 |
| 61 | 2-(4-methoxyphenyl)-4-phenylthiazole | 92 | | | 0 |
| 62 | 2-(4-methoxyphenyl)-4,5-diphenyl-thiazole | 97 | | 47 | 0 |
| 63 | 2,4,5-tris-(4-methoxyphenyl)thiazole | 78 | | | 10 |
| 64 | 2-(2,5-dimethoxyphenyl)-4-phenyl-thiazole | 100 | | 98 | 100 |
| 65 | 2-(2,5-dimethoxyphenyl)-4-(2,4-dimethylphenyl)thiazole | 100 | | 14 | 100 |
| 66 | 4-(4-chlorophenyl)-2-(2,5-dimethoxy-phenyl)thiazole | 75 | | | 10 |
| 67 | 2-(2,5-dimethoxyphenyl)-4,5-diphenyl-thiazole | 100 | 53 | 24 | 0 |
| 68 | 2-(3,4-dimethoxyphenyl)-4-phenyl-thiazole | 94 | | | 0 |
| 69 | 2-(4-ethoxy-3-methoxyphenyl)-4-phenyl-thiazole | 98 | 32 | 28 | 40 |
| 70 | 2-(3,4-dimethoxyphenyl)-4,5-diphenyl-thiazole | 90 | | | 85 |
| 71 | 2-(4-ethoxy-3-methoxyphenyl)-4,5-diphenyl-thiazole | 95 | | 60 | 0 |
| 72 | 5-(4-chlorophenyl)-2-(3,4-dimethoxyphenyl)-4-phenylthiazole | 95 | 86 | 84 | 0 |
| 73 | 2-(3,4-methylenedioxyphenyl)-4-phenyl-thiazole | 100 | 36 | 42 | 35 |
| 74 | 2-(3,4-methylenedioxyphenyl)-4,5-diphenyl-thiazole | 100 | | | 0 |
| 75 | 5-(2-chlorophenyl)-4-(3,4-dimethoxyphenyl)-2-(3-pyridyl)thiazole | 96 | 50 | 20 | 85 |
| 76 | 2-(3,4-dimethoxyphenyl)-5-methyl-4-phenyl-thiazole | 25 | | | 0 |
| 77 | 4-(4-fluorophenyl)-2-(3-methylphenyl)-thiazole | 25 | | | |
| 78 | 2-(4-chlorophenyl)-4-(4-fluorophenyl)-thiazole | 0 | | | |
| 79 | 4-(4-chlorophenyl)-2-(3,4-methylenedioxyphenyl)-thiazole | 0 | | | 0**** |
| 80 | 5-ethyl-2,4-diphenylthiazole | | | 0 | 75 |

TABLE 1-continued

| | | Adjusted Percent Control | | | |
|---|---|---|---|---|---|
| Compound No. | Compound Name | Mite Contact (1000 ppm) | Mite Residual (1000 ppm) | Mite Residual (500 ppm) | Mosquito Larvae (10 ppm) |
| 81 | 5-ethyl-2-(4-methoxyphenyl)-4-phenylthiazole | | | 0 | |

*and 97% control at 100 ppm and 100% control at 500 ppm
**and 44% control at 100 ppm and 84% control at 500 ppm
***100% control at 2000 ppm
****and 0% control at 100 ppm Having fully described our invention, we claim:

1. A method of controlling insect or acarid pests which comprises contacting the locus of said pests with an insecticidally or acaricidally effective amount of an aryl-substituted thiazole having the following structural formula:

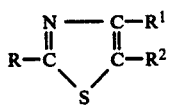

wherein R is selected from the group consisting of phenyl, alkylphenyl having 7 to 14 carbon atoms, aminophenyl, alkaminophenyl having 7 to 14 carbon atoms, halophenyl, and hydroxyphenyl; $R^1$ is selected from the group consisting of hydrogen, alkyl having 1 to 5 carbon atoms, phenyl, biphenylyl, aminophenyl, alkaminophenyl having 7 to 14 carbon atoms, alkylphenyl having 7 to 14 carbon atoms, and halophenyl; and $R^2$ is selected from the group consisting of hydrogen, alkyl having 1 to 5 carbon atoms, phenyl, halophenyl, and nitro; provided that two of R, $R^1$ and $R^2$ are aromatic.

2. The method of claim 1 wherein R is selected from the group consisting of phenyl, alkylphenyl having 7 to 9 carbon atoms, aminophenyl, alkaminophenyl having 7 to 8 carbon atoms, chlorophenyl, and hydroxyphenyl; $R^1$ is selected from the group consisting of hydrogen, methyl, ethyl, phenyl, biphenylyl, aminophenyl, alkaminophenyl having 7 to 8 carbon atoms, alkylphenyl having 7 to 9 carbon atoms, chlorophenyl, and bromophenyl; and $R^2$ is selected from the group consisting of hydrogen, methyl, phenyl, chlorophenyl, and nitro; provided that two of R, $R^1$ and $R^2$ are aromatic.

3. A method of controlling insect or acarid pests which comprises contacting the locus of said pests with an insecticidally or acaricidally effective amount of an aryl-substituted thiazole selected from the group consisting of:
  2,5-diphenylthiazole,
  4-methyl-2,5-diphenylthiazole,
  4-ethyl-2,5-diphenylthiazole,
  2,4-diphenylthiazole,
  5-methyl-2,4-diphenylthiazole
  5-(4-chlorophenyl)-4-methyl-2-(3-methylphenyl)-thiazole,
  5-methyl-2-(4-methylphenyl)-4-phenylthiazole,
  2-(2-chlorophenyl)-4-methyl-5-phenylthiazole,
  2-(2-chlorophenyl)-4-ethyl-5-phenylthiazole, and
  2-(4-chlorophenyl)-4-phenylthiazole.

4. A method of controlling acarid or insect pests which comprises contacting the said pests with an insecticidally or acaricidally effective amount of an aryl-substituted thiazole having the following structural formula:

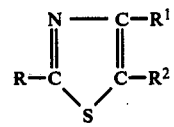

wherein R is selected from the group consisting of phenyl, alkylphenyl having 7 to 14 carbon atoms, aminophenyl, alkaminophenyl having 7 to 14 carbon atoms, halophenyl, and hydroxyphenyl; $R^1$ is selected from the group consisting of hydrogen, alkyl having 1 to 5 carbon atoms, phenyl, biphenylyl, aminophenyl, alkaminophenyl having 7 to 14 carbon atoms, alkylphenyl having 7 to 14 carbon atoms, and halophenyl; and $R^2$ is selected from the group consisting of hydrogen, alkyl having 1 to 5 carbon atoms, phenyl, halophenyl, and nitro; provided that only one of $R^1$ and $R^2$ is aromatic.

5. The method of claim 4 wherein R is selected from the group consisting of phenyl, alkylphenyl having 7 to 9 carbon atoms, aminophenyl, alkaminophenyl having 7 to 8 carbon atoms, chlorophenyl, and hydroxyphenyl; $R^1$ is selected from the group consisting of hydrogen, methyl, ethyl, phenyl, biphenylyl, aminophenyl, alkaminophenyl having 7 to 8 carbon atoms, alkylphenyl having 7 to 9 carbon atoms, chlorophenyl, and bromophenyl; and $R^2$ is selected from the group consisting of hydrogen, methyl, phenyl, chlorophenyl, and nitro; provided that only one of $R^1$ and $R^2$ is aromatic.

* * * * *